(12) United States Patent
Leverd et al.

(10) Patent No.: US 8,753,652 B2
(45) Date of Patent: Jun. 17, 2014

(54) PHARMACEUTICAL COMPOSITION INCLUDING A DHA ESTER TO BE ADMINISTERED PARENTERALLY

(75) Inventors: Elie Leverd, Castres (FR); Peter Van Hoogevest, Bubendorf (CH); Elsa Kung, Basel (CH); Mathew Leigh, Muttenz (CH)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/389,970

(22) PCT Filed: Aug. 11, 2010

(86) PCT No.: PCT/EP2010/061701
§ 371 (c)(1),
(2), (4) Date: Feb. 10, 2012

(87) PCT Pub. No.: WO2011/018480
PCT Pub. Date: Feb. 17, 2011

(65) Prior Publication Data
US 2012/0141563 A1 Jun. 7, 2012

(30) Foreign Application Priority Data
Aug. 11, 2009 (FR) ...................................... 09 55612

(51) Int. Cl.
*A61K 9/00* (2006.01)
*A61K 47/14* (2006.01)

(52) U.S. Cl.
CPC ...................................... *A61K 47/14* (2013.01)
USPC .......................................... 424/400; 424/484

(58) Field of Classification Search
CPC ........................... A61K 2300/00; A61K 47/14
USPC .................................................. 424/400, 484
See application file for complete search history.

(56) References Cited

U.S. PATENT DOCUMENTS 5,760,081 A * 6/1998 Leaf et al. .................... 514/560

FOREIGN PATENT DOCUMENTS

| CN | 101091890 A | 12/2007 |
|---|---|---|
| CN | 101259102 A | 9/2008 |
| EP | 2184100 A1 | 5/2010 |
| WO | WO 00/78795 A2 | 12/2000 |
| WO | WO 01/46115 A1 | 6/2001 |
| WO | WO 01/64328 A1 | 9/2001 |
| WO | WO 2004/032910 A1 | 4/2004 |
| WO | WO 2007/147899 A2 | 12/2007 |

OTHER PUBLICATIONS

Joshi et al., Title: "Design and in vivo pharmacodynamic evaluation of nanostructural lipid carriers for parenteral delivery of srtemeter: Nanoject", International Journal of Pharmaceutics; published Aug. 14, 2008 by Elsevier.*
Floyd A., Title: "Top ten considerations in the development of parenteral emulsions", PSTT, vol. 2, No. 4 pp. 134-143; published Apr. 1999 by Elsevier.*
Jumaa et al., Title: Parenteral emulsions stabilized with a mixture of phospholipids and PEG-660-12-hydroxy-stearate: evaluation of accelerated and long-term stability; European Journal of Pharmaceutics and Biopharmaceutics, vol. 54, Issue 2, Sep. 2002, pp. 207-212.*
DeMerlis et al., Title: The IPEC Novel Excipient Safety Evaluation Procedure; Pharmaceutical Technology, vol. 33, Issue 11, pp. 72-82, Nov. 2, 2009. Only relevant portion, Abstract, is attached.*
Definition of emulsion from e-Dictionary.*
Physical property of docosahexaenoic acid.*
Billman et al., "Prevention of Ischemia-Induced Cardiac Sudden Death by n-3 Polyunsaturated Fatty Acids in Dogs," Lipids, vol. 32, No. 11, 1997, pp. 1161-1168.
Jumaa et al., "Parenteral emulsions stabilized with a mixture of phospholipids and PEG-660-12-hydroxy-stearate: evaluation of accelerated and long-term stability," European Journal of Pharmaceutics and Biopharmaceutics, vol. 54, 2002, pp. 207-212, XP004377365.

* cited by examiner

*Primary Examiner* — Johann R Richter
*Assistant Examiner* — Yanzhi Zhang
(74) *Attorney, Agent, or Firm* — Birch, Stewart, Kolasch & Birch, LLP

(57) ABSTRACT

The present invention relates to a pharmaceutical composition to be parenterally administered, including submicronic ester particles of docosahexaenoic acid, dispersed in an aqueous phase using a mixture of at least two surfactants selected from among a) at least one polyoxyethylene fatty acid ester and b) at least one phospholipid derivative. The present invention also relates to the method for preparing said pharmaceutical composition.

11 Claims, 2 Drawing Sheets

PHARMACEUTICAL COMPOSITION INCLUDING A DHA ESTER TO BE ADMINISTERED PARENTERALLY

The present invention relates to a pharmaceutical composition to be administered parenterally, including a docosahexaenoic acid ester.

Omega 3 fatty acids are polyunsaturated fatty acids particularly found in algae, oily fish (salmon, mackerel, sardine, tuna), rapeseed, walnut, soy, etc. As a general rule, the classification of the fatty acids $CH_3-(CH_2)_n-COOH$ is based on the carbon chain length (short for n=2 to 4, medium for n=6 to 8 and long for n≥10), the number of double bonds (unsaturated, mono or polyunsaturated) and the position of the double bonds starting from the carbon in the carboxyl group. The ω reference system indicates the carbon chain length, the number of double bonds and the position of the closest double bond of the ω carbon starting from said ω carbon which is, by definition, the last carbon in the chain, furthest from the carboxyl group.

The main fatty acids in the ω 3 group are:
linolenic acid 18:3 (9, 12, 15) or ALA
eicosapentaeneoic acid 20:5 (5, 8, 11, 14, 17) or EPA
docosahexaenoic acid 22:6 (4, 7, 10, 13, 16, 19) or DHA Omega 3 fatty acids provide numerous beneficial effects for human health.

The patent application WO 01/46115 A1 summarises the benefits of a diet based on fish oil, rich in EPA and DHA, on reducing cardiovascular accidents. A parenteral form of EPA and DHA is mentioned therein, in the form of a globular particle suspension obtained using methods well known to those skilled in the art for example by diluting a non-ionic detergent surfactant in water, heating same and adding DHA and EPA ester. This application also describes emulsions intended to be administered intravenously containing soybean oil and triglycerides via the citation of publication on page 8 line 2 (Billman et al. 1997 Lipids 32 1161-1168).

However, using such a process, it is difficult to obtain stable parenteral formulations ready for use, or to be reconstituted using the freeze-dried form, wherein the mean particle size is less than 100 nm, for incorporating a large quantity of active ingredient and not containing an excessively high proportion of surfactant which may prove to be toxic in the long term.

Of the DHA esters, nicotinic ester or pyridin-3-ylmethyl-cis-4,7,10,13,16,19-docosahexaenoic acid is an ester of considerable therapeutic interest.

The structural formula of the nicotinic ester of DHA or pyridin-3-ylmethyl-cis-4,7,10,13,16,19-docosahexaenoic acid is given below:

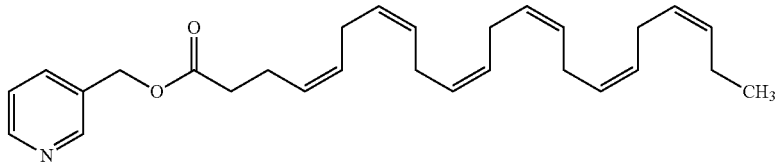 [SMILES: CC/C=C\C/C=C\C/C=C\C/C=C\C/C=C\C/C=C\CCC(=O)OCc1cccnc1]

The molecular weight is 419.60 g, corresponding to $C_{28}H_{37}NO_2$.

It is a very lipophilic compound (Log P approximately 7), wherein the solubility at equilibrium in water is <1 μg/ml. It is thus particularly difficult to formulate for parenteral administration.

A further DHA ester of particular interest is the panthenol ester of DHA, otherwise referred to as panthenyl docosahexaenoate, in particular the panthenol monoester of DHA 2,4-dihydroxy-3,3-dimethylbutanamido) propyl docosa 4,7,10,13,16,19-hexanoate, having the following formula A:

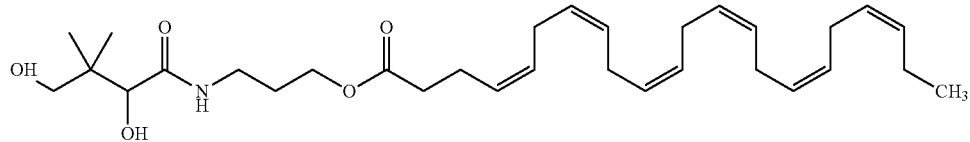 [SMILES: CC/C=C\C/C=C\C/C=C\C/C=C\C/C=C\C/C=C\CCC(=O)OCCCNC(=O)C(O)C(C)(C)CO]

or any of the pharmaceutical acceptable salts, enantiomers, diastereoisomers thereof, or mixture thereof, including racemic mixtures.

More specifically, the ester may be the panthenol monoester of DHA having the following formula B:

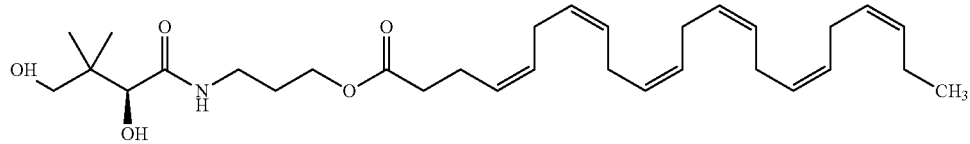 [SMILES: CC/C=C\C/C=C\C/C=C\C/C=C\C/C=C\C/C=C\CCC(=O)OCCCNC(=O)[C@@H](O)C(C)(C)CO]

otherwise referred to as "D-panthenol DHA ester".

These esters are very effective for example in treating atrial fibrillation as described in WO 2007/147899. They act as a prodrug, releasing DHA into the body, after hydrolysis.

In the present invention, the term "enantiomers" refers to optical isomeric compounds which have identical molecular formulas but which differ by the spatial configuration thereof and which are non-superimposable mirror images. The term "diastereoisomers" refers to optical isomers which are not mirror images of each other. According to the present invention, a "racemic mixture" is a mixture of equal proportions of the levorotatory and dextrorotatory enantiomers of a chiral molecule.

In the present invention, the term "pharmaceutical acceptable" or "acceptable in pharmaceutical terms" refers to that which is suitable for use in the preparation of a pharmaceutical composition which is generally safe, non-toxic and not biologically or otherwise undesirable and which is acceptable for both veterinary and human pharmaceutical use.

The term "pharmaceutically acceptable salts" of a compound refers to salts which are pharmaceutically acceptable, as defined herein, and which have the desired pharmacological activity of the parent compound. Such salts include:

(1) acid addition salts formed with mineral acids such as hydrochloric acid, hydrobromic acid, sulphuric acid, nitric acid, phosphoric acid and similar; or formed with organic acids such as acetic acid, benzenesulphonic acid, benzoic acid, camphorsulphonic acid, citric acid, ethane-sulphonic acid, fumaric acid, glucoheptonic acid, gluconic acid, glutamic acid, glycolic acid, hydroxynaphthoic acid, 2-hydroxyethane-sulphonic acid, lactic acid, maleic acid, malic acid, mandelic acid, methanesulphonic acid, muconic acid, 2-naphthalene sulphonic acid, propionic acid, salicylic acid, succinic acid, dibenzoyl-L-tartaric acid, tartaric acid, p-toluene sulphonic acid, trimethyl acetic acid, trifluororacetic acid and similar; or (2) salts formed when an acid proton present in the parent compound either is replaced by a metallic ion, for example an alkaline metal ion, an alkaline-earth metal ion or an aluminium ion; or is arranged with an organic or inorganic base. Acceptable organic bases include diethanolamine, ethanolamine, N-methylglucamine, triethanolamine, tromethamine and similar. Acceptable inorganic bases include aluminium hydroxide, calcium hydroxide, potassium hydroxide, sodium carbonate and sodium hydroxide.

The preferred pharmaceutically acceptable salts are sales formed from hydrochloric acid, trifluoroacetic acid, dibenzoyl-L-tartaric acid and phosphoric acid.

It should be understood that any references to pharmaceutically acceptable salts include the solvent addition forms (solvates) or crystalline forms (polymorphs) as defined herein, of the same acid addition salt.

The inventors unexpectedly discovered that it was possible to prepare compositions including a DHA ester to be administered parenterally, using an association of two types of surfactants, a polyoxyethylene fatty acid ester and a phospholipid derivative.

The present invention thus relates to a pharmaceutical composition to be administered parenterally, including submicronic ester particles of docosahexaenoic acid, dispersed in an aqueous phase using a mixture of at least two surfactants selected from a) at least one polyoxyethylene fatty acid ester and b) at least one phospholipid derivative.

According to one embodiment of the invention, the composition only contains the two types of surfactants a) and b) as the surfactant.

The docosahexaenoic acid ester may be of any type. It may in particular be an ethyl ester or an ester with a vitamin B as described in patent application WO 2007/147899.

In one embodiments of the invention, it is the nicotinic ester of DHA, i.e. pyridin-3-ylmethyl-cis-4,7,10,13,16,19-docosahexaenoic acid, or the panthenol ester of DHA, in particular the panthenol monoester of DHA 2,4-dihydroxy-3,3-dimethylbutanamido) propyl docosa 4,7,10,13,16,19-hexanoate, and more particularly D-panthenol DHA ester, which are particularly difficult to formulate for parenteral administration.

In one embodiment of the present invention, the docosahexaenoic acid ester concentration is greater than or equal to 10 mg/ml, for example, greater than or equal to 30 mg/ml.

The first surfactant agent (a) belongs to the group of polyoxyethylene fatty acid esters. The polyoxyethylene fatty acid esters may be obtained by means of a reaction between a fatty acid and an ethylene oxide or a polyethylene glycol.

In particular, the polyoxyethylene fatty acid esters according to the invention have the following formula (1) or (2):

wherein R, $R_1$ and $R_2$ represent independently of each other the alkyl or alkenyl group of the parent fatty acid and n represents the polymer chain length, in oxyethylene structural units. For example, n is between 10 and 60, for example between 12 and 20, for example 15.

The fatty acid may be saturated or unsaturated. It is hydroxylated. The most common saturated fatty acids are as follows:

| Common name | IUPAC name | Chemical structure | Abbr. | Melting point (°C.) |
|---|---|---|---|---|
| Butyric | butanoic acid | $CH_3(CH_2)_2COOH$ | C4:0 | −8 |
| Caproic | hexanoic acid | $CH_3(CH_2)_4COOH$ | C6:0 | −3 |
| Caprylic | octanoic acid | $CH_3(CH_2)_6COOH$ | C8:0 | 16-17 |
| Capric | decanoic acid | $CH_3(CH_2)_8COOH$ | C10:0 | 31 |
| Lauric | dodecanoic acid | $CH_3(CH_2)_{10}COOH$ | C12:0 | 44-46 |
| Myristic | tetradecanoic acid | $CH_3(CH_2)_{12}COOH$ | C14:0 | 58.8 |
| Palmitic | hexadecanoic acid | $CH_3(CH_2)_{14}COOH$ | C16:0 | 63-64 |
| Stearic | octadecanoic acid | $CH_3(CH_2)_{16}COOH$ | C18:0 | 69.9 |
| Arachidic | eicosanoic acid | $CH_3(CH_2)_{18}COOH$ | C20:0 | 75.5 |
| Behenic | docosanoic acid | $CH_3(CH_2)_{20}COOH$ | C22:0 | 74-78 |
| Lignoceric | Tetracosanoic acid | $CH_3(CH_2)_{22}COOH$ | C24:0 | |

Consequently, R, $R_1$ or $R_2$ is, for example, an alkyl or alkenyl chain, e.g. alkyl, linear or branched, for example linear, in $C_3$-$C_{23}$, for example in $C_{11}$-$C_{23}$, for example in $C_{15}$-$C_{21}$, for example, the fatty acid is a long-chain saturated fatty acid, i.e. having more than 16 carbon atoms.

In one embodiment, the fatty acid has between 12 and 24 carbon atoms, for example, between 14 and 22 carbon atoms, for example between 16 and 20 carbon atoms, for example, it has 18 carbon atoms, for example, it is stearic acid.

It may be a fatty acid mono or diester, or a mixture thereof. In one embodiment of the invention, it is a mixture of fatty acid mono or diester. For example, the polyoxyethylene fatty acid ester is macrogol-15 hydroxystearate (trade name:

SOLUTOL HS15, manufacturer: BASF, Ludwigshafen, Germany). It is a non-ionic solubilising agent, essentially consisting of monoesters and diesters of 12-hydroxystearic acid and macrogols obtained by ethoxylation of 12-hydroxystearic acid. The number of moles of ethylene oxide reacting per mole of 12-hydroxystearic acid is 15. It is in the form of a yellowish waxy mass, very soluble in water.

In particular, the polyoxyethylene fatty acid esters suitable for use within the scope of the present invention are non-ionic surfactants.

The second surfactant agent (b) belongs to the group of phospholipid derivatives: it may thus consist of lecithins of natural origin, such as for example soy or egg lecithins, phospholipids of natural origin, such as for example soy or egg phospholipids, or synthetic phospholipids, or a mixture thereof. For example, it may consist of neutral phospholipids such as phosphatidylcholines, such as for example 1,2-dimyristoylphosphatidylcholine or 1-palmitoyl-2-oleoylphosphatidylcholine, and phosphatidylethanolamines, for example phosphatidylcholines, negatively charged phospholipids such as phosphatidylglycerols, such as for example 1,2-dimyristoylphosphatidylglycerol, phosphatidylserines, phosphatidylinositols and phosphatidic acids, e.g. phosphatidylglycerols, or mixtures thereof. For example, it may consist of a neutral phospholipid such as a phosphatidylcholine, or it may consist of a mixture of a neutral phospholipid and a negatively charged phospholipids, for example 1-palmitoyl-2-oleoylphosphatidylcholine and 1,2-dimyristoylphosphatidylglycerol.

In the mixture of a neutral phospholipid and a negatively charged phospholipid, the percentage by mass of negatively charged phospholipids with reference to the total composition of the mixture is less than 10%, between 1% and 5%, e.g. equal to 3%.

It may also consist of a mixture of a lecithin of natural origin with a negatively charged phospholipid, in particular an egg lecithin with 1,2-dimyristoylphosphatidylglycerol.

The mass ratio of type a) surfactant:type b) surfactant may be between 1:3 and 3:1, for example, it is 1:1.

The phospholipid derivatives have the general structure indicated in FIG. 1.

In one embodiment of the invention, the phospholipid derivative does not contain soy lecithin or soy phospholipids.

In one embodiment, the submicronic particles are submicronic particles such as mixed micelles or vesicles or micellar or vesicular structure hybrids.

A mixed micelle according to the invention is a micelle, for example an aggregate, consisting of a mixture of the two different types of surfactants (a) and (b), the hydrophilic polar head of the surfactant molecules being directed towards the aqueous phase and the hydrophobic chain directed inwards, in interaction with the DHA ester.

A vesicle according to the invention is a structure wherein the surfactants are organised according to a bi-layer arrangement identical to that found in cell membranes. These surfactants surround a vacuole or aqueous cavity.

A micellar and vesicular structure hybrid according to the invention is an intermediate structure between a mixed micelle and vesicle, optionally with the existence of said vacuole.

In this way, for example, the composition according to the invention is a dispersion of mixed micelles or vesicles or micellar and vesicular structure hybrids. For example, these particles display plane fracture faces under an electronic microscope after cryofracture.

According to one embodiment of the present invention, the composition according to the invention is not in the form of an emulsion.

In one embodiment of the present invention, the submicronic particles have a mean size<100 nm, for example between 25 and 70 nm, for example with a polydispersity<0.5, (the size and polydispersity are determined by spectroscopy by photon correlation on a Malvern Zetasizer unit).

In addition to the submicronic particles described above, the composition according to the invention may also contain, optionally:

antioxidant agents protecting the DHA ester, particularly the nicotinic ester or panthenol ester of DHA, and in particular D-panthenol DHA ester, from oxidation by the oxygen dissolved in the composition. Non-limitative examples include: ascorbic acid and the derivatives thereof, compounds releasing sulphur dioxide such as sodium metabisulphite, propyl gallate, butylhydroxytoluene, butylhydroxyanisole, D,L-α-tocopherol, ethylenediaminetetraacetic acid derivatives and the combinations thereof. The content thereof is between 0.01% and 1% (m/V), more specifically between 0.01% and 0.50% (m/V). The action of the antioxidant agents is supplemented appropriately using inert gases such as nitrogen or argon during the production and packaging of the compositions for injection.

pH regulating agents. These are known to those skilled in the art and include mineral or organic acids and bases, and buffer systems. The use thereof makes it possible to set the pH of the composition according to the invention to a value between pH=4 and pH=9, compatible with parenteral administration. It may thus consist of ascorbic acid.

agents for adjusting the osmolarity of the composition according to the invention so as to ensure the isotonicity thereof with blood. These are, for example, neutral molecules such as carbohydrates, e.g. optionally reduced monosaccharides [for example glucose or mannitol at a concentration≤5% (m/V)] or disaccharides [for example sucrose at a concentration≤10% (m/V)].

water for injections as a dispersion medium, for example a 5% glucose solution or a 0.9% sodium chloride solution.

The compositions according to the invention are in the form of aqueous dispersions ready for administration or in the form of freeze-dried dispersions which are reconstituted extemporaneously with water for injections before administration.

In a non-limitative example, for a concentration of 30 ng/ml—or 3% (m/V)—of nicotinic ester of DHA, the concentrations of SOLUTOL HS15 and phospholipid derivative are between 2.5 and 5% (m/V) and 0 and 10% (m/V), respectively. Preferentially, a composition with 5% (m/V) of SOLUTOL HS15 and 5% (m/V) of phospholipid derivative will be used.

The formulations given in table 1 below illustrate the present invention. They were prepared using the first process described hereinafter.

|  | 1 | 2 | 3 | 4 |
|---|---|---|---|---|
| nicotinic ester of DHA | 3.00 g | 3.00 g | 3.00 g | 3.00 g |
| 1,2-Dimyristoylphosphatidylcholine | 5.00 g | | | |

-continued

|  | 1 | 2 | 3 | 4 |
|---|---|---|---|---|
| 1-Palmitoyl-2-oleoylphosphatidyl-choline |  | 4.85 g | 4.85 g |  |
| 1,2-Dimyristoylphosphatidylglycerol |  | 0.15 g | 0.15 g | 0.15 g |
| Egg lecithin |  |  |  | 4.85 g |
| SOLUTOL HS15 | 5.00 g | 5.00 g | 5.00 g | 5.00 g |
| Ascorbic acid |  |  | 0.20 g |  |
| 5% glucose solution | up to 100 ml | up to 100 ml | up to 100 ml | up to 100 ml |
| Mean particle size | 28.6 nm | 52.0 nm | 65.1 nm | 50.6 nm |
| Polydispersity | 0.4 | 0.3 | 0.1 | 0.2 |

The present invention further relates to a process for preparing the composition according to the present invention including the following steps:
  dispersing the DHA ester, in particular the nicotinic ester of DHA or panthenol ester of DHA, in particular the panthenol monoester of DHA having formula A or formula B, the phospholipid derivative(s) and the polyoxyethylene fatty acid ester, for example SOLUTOL HS15, in an aqueous solution to be administered parenterally, e.g. a 5% glucose solution, under stirring for example magnetic or anchor stirring, for example at approximately 700 rpm, until a homogeneous but cloudy dispersion is obtained,
  homogenising the dispersion obtained, for example using a rotor/stator turbine (for example Labortechnik T25 (IKA) type or equivalent), e.g. at approximately 13,500 rpm, followed by a high-pressure homogeniser (for example EMULSIFLEX C-5 (AVESTIN) type or equivalent), e.g. at a pressure between 1300 and 1600 bar,
  sterilising the colloidal formulation obtained, for example by passing through a 0.2 µm sterilising filter such as the MILLIPORE DURAPORE® type or equivalent.

The process may further include a further step consisting of filling the sterile filtrate, in an aseptic atmosphere, in clean and previously sterilised primary packaging materials.

This primary packaging is for example either a sealed vial, or a flask sealed with an elastomer stopper and a crimping cap, or a pre-filled syringe ready to be administered.

In an alternative process, both surfactants a) and b) may be previously co-homogenised in an aqueous solution to be administered parenterally such as a 5% glucose solution, before adding the DHA ester, in particular the nicotinic ester or panthenol ester of DHA, in particular the panthenol monoester of DHA having formula A or formula B and final homogenisation.

In a further alternative process, the surfactant a) and the DHA ester are homogenised prior to adding the surfactant b) followed by the homogenisation of the whole. A solvent is then added, for example, an alcohol/water mixture, for example ethanol/water, for example 15.8:1 v/v respectively, and the homogenisation is continued. The solvent is then removed by vacuum-drying. The complex obtained is then diluted in a 5% glucose solution. The dispersion obtained is optionally homogenised, for example using a high-pressure homogeniser. The formulation obtained is sterilised by passing through a 0.22 µm filter, as described above.

Any antioxidant agents, pH-regulating agents and/or isotonic agents are dissolved in the aqueous phase either before or after homogenisation.

In one embodiment, the pharmaceutical composition according to the invention is intended for intravenous, intra-arterial, intracardiac, subcutaneous, intradermal, intramuscular, intrarachidian, intrathecal, intraperitoneal, intraocular, intraventricular, intrapericardial, intradural or intra-articular administration.

As a general rule, the compositions according to the invention are administered intravenously, as is or after dilution in physiologically acceptable solutions such as 5% glucose solutions or 0.9% sodium chloride solutions.

These compositions may also be administered by the intraarterial, intracardiac, subcutaneous, intradermal, intramuscular or intrarachidian route.

The present invention further relates to a pharmaceutical composition according to the invention, for use as a medicinal product.

The medicinal product is intended for the prevention and/or treatment of cardiovascular diseases, for example selected from supraventricular and/or ventricular arrhythmia, tachycardia and/or fibrillation, e.g. atrial fibrillation; for the prevention and/or treatment of diseases represented by myocardial cell electrical conduction defects; for the prevention and/or treatment of multiple risk factors of cardiovascular diseases, for example selected from hypertriglyceridaemia, hypercholesterolaemia, hyperlipidaemia, dyslipidaemia, e.g. mixed dyslipidaemia, arterial and venous thrombosis induced by blood clotting and/or platelet aggregation factor II (thrombin) hyperactivity, and/or arterial hypertension; for the primary or secondary prevention and/or treatment of cardiovascular diseases derived from supraventricular and/or ventricular arrhythmia, tachycardia, fibrillation and/or electrical conduction defects induced by myocardial infarction, advantageously sudden death; and/or for post-infarction treatment.

The invention will be understood more clearly in the light of the figures and tests on atrial fibrillation hereinafter:

EXAMPLE 1

Figure 1:
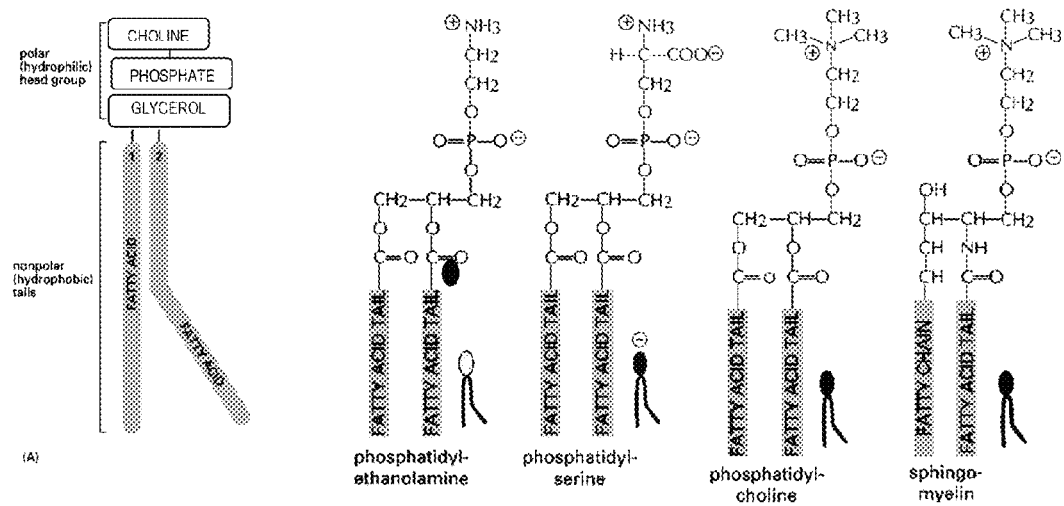
FIG. 1 represents the general structure of the phospholipid derivatives.

For example, the activity of the compositions according to the invention given in table 1 in the treatment of atrial fibrillation is perfectly demonstrated by the pharmacological test described hereinafter.

Male Landrace pigs (22-25 kg) are anaesthetised with isoflurane (1.5-3%). The animals are then intubated and ventilated to keep the arterial gas values within physiological limits. A left thoracotomy is performed at the fourth intercostal space. The artery and the mammary vein are isolated, catheters are inserted into the vein to administer the products under test and in the artery to measure the arterial pressure and collect blood samples. A pericardial bed is performed. An atrial electrocardiogram (ECG) is recorded continuously, three electrodes are placed on the epicardium and sutured. For this reason, the ECG only provides information on the atrial stage. Two bipolar electrodes are also placed on the left auricle: they will be used to stimulate the auricle electrically at a given frequency.

Experimental Protocol:

After a sufficient recovery period, the determination of the atrial refractory period under controlled conditions can begin. A continuous series of stimuli (S1) is started at a very low voltage (0.1 V), insufficient to stimulate the heart. The voltage is progressively increased (in 0.1 V intervals) to determine the stimulation threshold for monitoring the frequency applied. This threshold is determined at each stimulation frequency. There are 4 stimulation frequencies, 90, 120, 150 and 180 bpm. If the pig has a baseline heart rate greater than 90 bpm, the first stimulation frequency is not applied. Similarly, if the baseline rate is low (<90 bpm), the final stimulation frequency (180 bpm) tested does not always stimulate the heart. Once the threshold has been determined, the voltage of the stimulation S1 (series of 10 stimuli) is equal to twice the threshold, and the voltage of the extrastimulus S2 is equal to 4 times the threshold. Every 10 S1, an extrastimulus S2 is triggered during the refractory period (i.e. 80 ms after the final S1, the expected refractory period is at least 100 ms), and every 10 stimuli S1, the extrastimulus is separated from the final S1 (5 ms increment) until it engages a beat itself. The longest interval not inducing a response to S2 is the atrial refractory period. The refractory period is evaluated 3 times in succession (expression of the mean), at 4 different stimulation frequencies, i.e. 12 measures. The product under test is administered in the form of a bolus and infusion over 40 min (time required to evaluate all the refractory periods). The thresholds are not recalculated, the refractory periods are measured immediately (5 min after the end of the bolus). If the product is active, the refractory periods should be increased with respect to the control phase.

Figure 2:
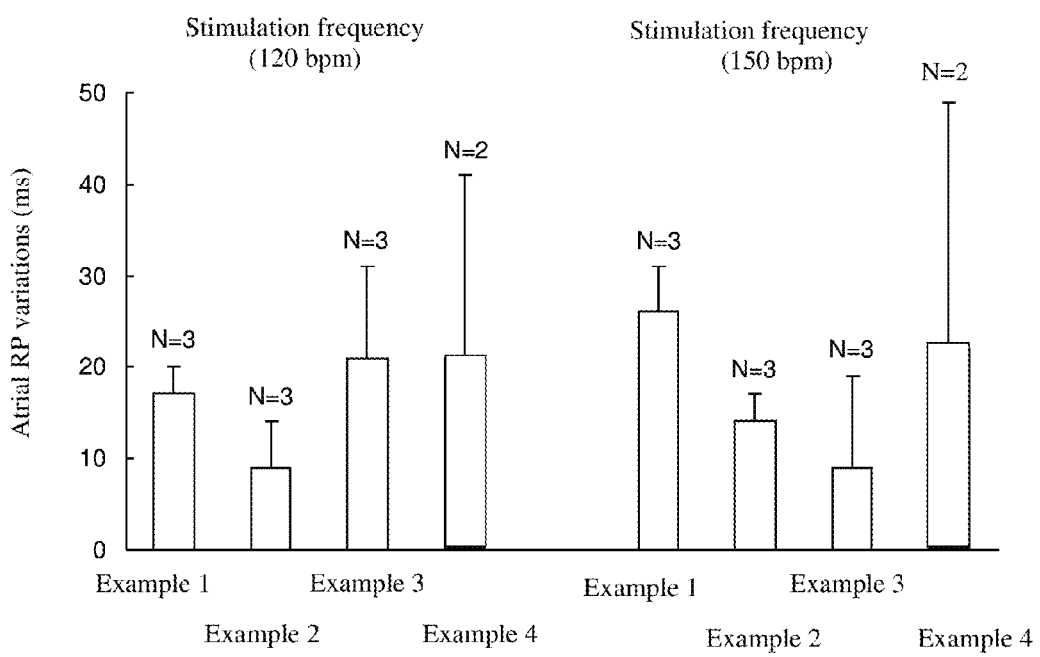
FIG. 2 represents the measurement of the atrial refractory periods in anaesthetised pigs following the administration of the compositions according to the invention (10 mg/kg bolus of nicotinic ester of DHA+10 mg/kg infusion of nicotinic ester of DHA over 40 minutes) with a stimulation frequency of 120 bpm and 150 bpm.
Figure 3:
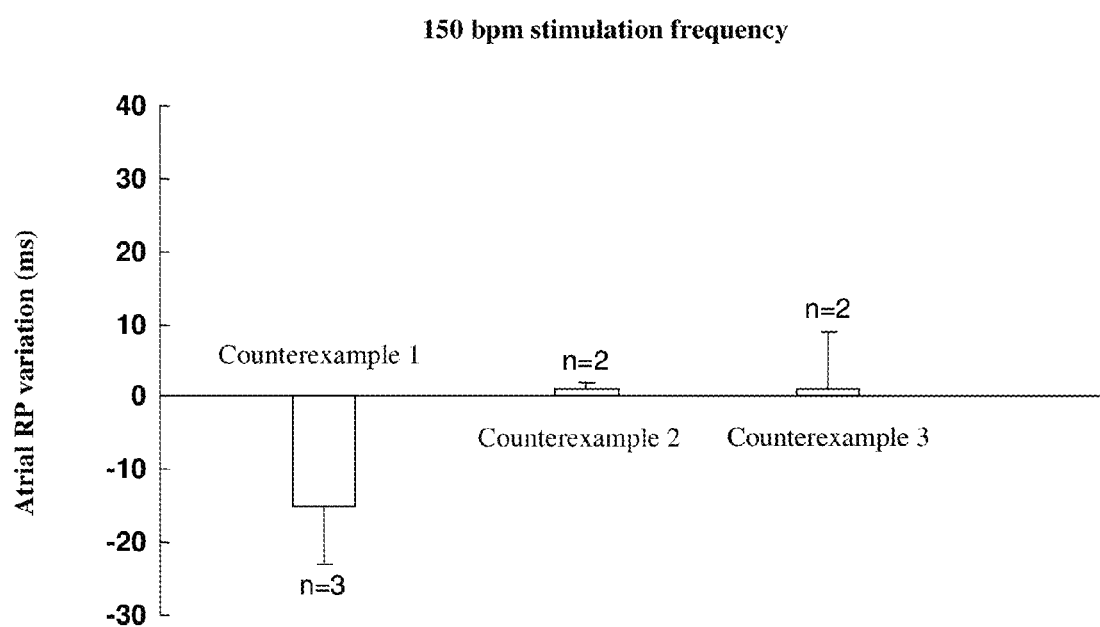
FIG. 3 represents the measurement of the atrial refractory periods in anaesthetised pigs following the administration of comparative compositions (counterexamples) (10 mg/kg bolus of nicotinic ester of DHA+10 mg/kg infusion of nicotinic ester of DHA over 40 minutes) with a stimulation frequency of 150 bpm.

It should be noted that only the compositions according to the invention respond positively to this pharmacological test as illustrated by FIGS. 2 and 3.

The counterexamples are formulations very similar to the formulations according to the invention as indicated in table 2 below, but they display an inferior or negative pharmacological activity.

TABLE 2

| | Counter-example 1 | Counter-example 2 | Counter-example 3 |
|---|---|---|---|
| nicotinic ester of DHA | 3.00 g | 3.00 g | 3.00 g |
| 1,2-Dimyristoylphosphatidylcholine | | | 2.00 g |
| SOLUTOL HS15 | 5.00 g | | |
| Polysorbate 80 | | 2.50 g | |
| Medium-chain triglycerides | | 2.50 g | |
| 1,2-Dimyristoylphosphatidylglycerol | | | 0.50 g |
| 5% glucose solution | up to 100 ml | up to 100 ml | up to 100 ml |

Therefore, it is noted that the absence of one of the surfactants ((a) or (b), respectively counterexample 3 and counterexample 1) in the composition to be administered parenterally containing the nicotinic ester of DHA or the use of another surfactant than a) or b) (counterexample 2) does not make it possible to obtain the desired activity.

EXAMPLE 2

Formulation for Injection Including the Panthenol Ester of DHA Having Formula B

POPC=1-palmitoyl-2-oleoyl phosphatidylcholine
EPCS=egg phosphatidyl choline
DMPG=1,2,dimyristoylphosphatidylglycerol 1—Preparation Process by Complexing in the Presence of Solvent:

Solutol HS15 and the panthenol ester of DHA having formula B are mixed at a temperature of 50° C. until homogenised. The phospholipids are then added and the mixture is placed under magnetic stirring at a temperature of 50° C. for 1 hr to 1 hr 30 in an inert atmosphere for example, in nitrogen. Ethanol and water, for example, ethanol/water [15.8:1 v/v], are added to the mixture and the stirring is continued in an inert atmosphere until the lipids are completely dispersed. The mixture is then treated for 30 min by ultrasonication to obtain the complete dispersion of the phospholipids. The resulting dispersion is placed in a vacuum for at least 24 hrs to remove the solvent and water.

The complex is diluted in a 5% glucose solution. If the dispersion is opaque, it is homogenised with a high-pressure homogeniser until the dispersion is translucent and clear. It is sterilised on a 0.22 µm PVDF filter.

2—Preparation Process by Mixing Panthenol Ester of DHA with a Dispersion of Phospholipids and Solutol HS15.

The phospholipids, Solutol HS15 and the 5% glucose solution are weighed and the mixture is stirred magnetically and heated to 60° C. until a dispersion is obtained. The dispersion is then cycled with a high-pressure homogeniser until a clear and/or translucent dispersion is obtained.

The panthenol ester of DHA having formula B is then added to said dispersion and the mixture is homogenised for 1 to 2 minutes at 13,500 rpm. The dispersion is cycled in a high-pressure homogeniser under a clear and/or translucent dispersion is obtained, for example not more than 5 cycles. The dispersion is filtered through a 0.22 µm PVDF filter.

3—Preparation Process by Mixing Panthenol Ester of DHA, Phospholipids and Solutol HS15.

All the ingredients are weighed in a flask, a bar magnet is added and the flask is sealed in an inert atmosphere, for example in nitrogen. The mixture is stirred for 30 min or until a homogenous dispersion is obtained. The dispersion is homogenised at 13,500 rpm for 1 to 2 minutes and treated with a high-pressure homogeniser until a translucent and/or clear dispersion or a constant transmission is obtained, for example after 6 cycles. The formulations are filtered on 0.22 µm filters and the visual aspect, appearance under a microscope, pH, transmission and particle size are determined at T0 and after storage for 2 weeks at 4° C., 25° C. and 40° C.

The formulation was developed with the following compositions given in table 3 below:

TABLE 3

| | 30 mg P-DHA/ml POPC formulation | | 30 mg P-DHA/ml EPCS formulation | |
|---|---|---|---|---|
| Compounds | weight | Concentration (mg/ml) | weight | Concentration (mg/ml) |
| Panthenol ester of DHA having formula B | 3.00 | 30.1 | 3.00 | 30.1 |
| Solutol HS15 | 5.00 | 49.8 | 5.00 | 49.8 |
| POPC | 4.85 | 48.5 | — | — |
| EPCS | — | — | 4.85 | 48.5 |
| DMPG | 0.15 | 1.6 | 0.15 | 1.6 |
| 5% glucose solution | 87.00 | 870.1 | 87.00 | 870.1 |
| Total | 100 | 1000.1 | 100 | 1000.1 |

The examples above were used to assess whether the panthenol ester of DHA, for example the panthenol ester having formula B, can be combined directly with the excipients to form a complex which can subsequently be diluted with a 5% glucose solution to give a dispersion suitable for injection.

The composition obtained according to each of the 3 preparation processes is analysed.

The visual aspect and the appearance of the formulation are observed under a microscope, the pH, transmission and particle size are measured at T0 and after storage for 2 to 4 weeks at 4, 25 and 40° C.

The conclusion from these observations is that compositions containing 30 mg of panthenol ester of DHA having formula B per ml of Solutol HS15 and POPC or EPCS with DPMG and a 5% glucose solution can be prepared according to the three processes described. The pH remained stable over the two weeks, the particle size remained less than 100 nm. No degradation peak was observed on the HPLC chromatograms.

The invention claimed is:

1. A pharmaceutical composition to be administered parenterally, including submicronic ester particles of docosahexaenoic acid having a mean size <100 nm with a polydispersity <0.5, said particles being dispersed in an aqueous phase using a mixture of at least two surfactants selected from a) at least one polyoxyethylene fatty acid ester and b) at least one phospholipid, wherein the ester of docosahexaenoic acid is the panthenol ester of DHA having the following formula A:

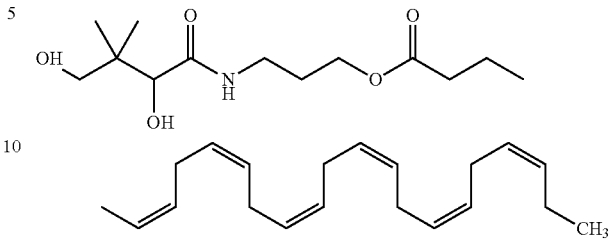

or any of the pharmaceutical acceptable salts, enantiomers, diastereoisomers thereof, or mixture thereof including racemic mixtures, or the ester of docosahexaenoic acid is the nicotinic ester, and wherein said composition is a dispersion of mixed micelles or vesicles or micellar and vesicular structure hybrids.

2. The pharmaceutical composition according to claim 1, characterised in that the ester of docosahexaenoic acid is the D enantiomer of the panthenol ester of DHA having the following formula B:

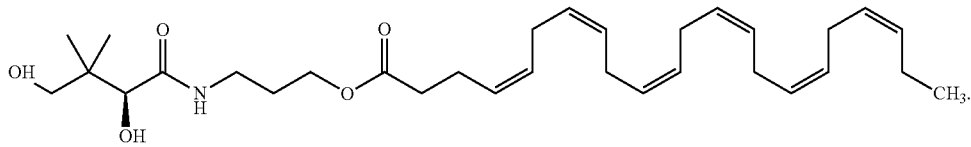 [SMILES: CC/C=C\C/C=C\C/C=C\C/C=C\C/C=C\C/C=C\CCC(=O)OCCCNC(=O)[C@@H](O)C(C)(C)CO]

3. The pharmaceutical composition according to claim 1 or to claim 2, characterised in that the polyoxyethylene fatty acid ester is macrogol-15 hydroxystearate.

4. The pharmaceutical composition according to claim 1, characterised in that the phospholipid is selected from lecithins of natural origin, phospholipids of natural origin, or synthetic phospholipids, or a mixture thereof.

5. The pharmaceutical composition according to claim 4, characterised in that the phospholipid is a mixture of a neutral phospholipid and a negatively charged phospholipid.

6. The pharmaceutical composition according to claim 1, characterised in that the docosahexaenoic acid ester concentration is greater than or equal to 10 mg/ml.

7. The pharmaceutical composition according to claim 1, characterised in that it is intended for intravenous, intraarterial, intracardiac, subcutaneous, intradermal, intramuscular, intrarachidian, intrathecal, intraperitoneal, intraocular, intraventricular, intrapericardial, intradural or intra-articular administration.

8. The pharmaceutical composition according to claim 1, for use as a medicinal product.

9. The pharmaceutical composition according to claim 4, wherein the lecithins of natural origin are soy or egg lecithins and the phospholipids of natural origin are soy or egg phospholipids.

10. The pharmaceutical composition according to claim 6, wherein the docosahexaenoic acid ester concentration is greater than or equal to 30 mg/ml.

11. The pharmaceutical composition according to claim 1, wherein the submicronic particles have a mean size between 25 nm and 70 nm, with a polydispersity <0.5.

* * * * *